United States Patent [19]

Colodney et al.

[11] Patent Number: 5,108,734

[45] Date of Patent: Apr. 28, 1992

[54] PROPHY MOUTHFEEL DENTIFRICE HAVING LOW RDA VALUE

[75] Inventors: Daniel Colodney, Hampton; Kathleen P. Thomas, Somerset, both of N.J.

[73] Assignee: Colgate-Palmolive Company, Piscataway, N.J.

[21] Appl. No.: 724,247

[22] Filed: Jul. 1, 1991

[51] Int. Cl.$^5$ .............................................. A61K 7/16
[52] U.S. Cl. ...................................................... 424/49
[58] Field of Search ................................... 424/49-58

[56] References Cited

U.S. PATENT DOCUMENTS

| | | | |
|---|---|---|---|
| 3,689,637 | 9/1972 | Poder | 424/52 |
| 3,943,240 | 3/1976 | Delaney et al. | 424/49 |
| 3,978,205 | 8/1976 | Newman et al. | 424/49 |
| 4,007,260 | 2/1977 | Patimo et al. | 424/52 |
| 4,108,978 | 8/1978 | Mazzanobile et al. | 424/49 |
| 4,110,083 | 8/1978 | Benedict | 51/295 |
| 4,141,969 | 8/1979 | Mitchell | 424/52 |
| 4,174,387 | 11/1979 | Cordon et al. | 424/49 |
| 4,303,641 | 12/1981 | De Wolf et al. | 424/49 |
| 4,346,071 | 8/1982 | Dent et al. | 424/49 |
| 4,401,648 | 8/1983 | Piechota | 424/49 |
| 4,474,824 | 10/1984 | De Wolf et al. | 424/49 |
| 4,631,184 | 12/1986 | Winyall et al. | 424/49 |
| 4,663,153 | 5/1987 | Winston | 424/52 |
| 4,689,216 | 8/1987 | Greene | 424/58 |
| 4,828,833 | 5/1989 | Cordon | 424/54 |
| 4,891,211 | 1/1990 | Winston | 424/52 |
| 4,894,220 | 1/1990 | Nabi et al. | 424/49 |
| 4,895,720 | 1/1990 | Ladas et al. | 424/49 |
| 4,943,429 | 7/1990 | Winston et al. | 424/52 |
| 4,956,167 | 9/1990 | Aldcroft et al. | 424/49 |
| 4,992,251 | 2/1991 | Aldcroft et al. | 424/49 |
| 5,028,413 | 7/1991 | Bianchi et al. | 424/49 |
| 5,035,879 | 7/1991 | Aldcroft et al. | 424/49 |

FOREIGN PATENT DOCUMENTS

| | | |
|---|---|---|
| 255000 | 2/1988 | European Pat. Off. |
| 268763 | 6/1988 | European Pat. Off. |
| 405682 | 1/1991 | European Pat. Off. |
| 2063667 | 6/1981 | United Kingdom |

*Primary Examiner*—Shep K. Rose
*Attorney, Agent, or Firm*—Paul Shapiro; Robert C. Sullivan

[57] ABSTRACT

A dentifrice cream composition and the process for its preparation is disclosed. The dentifrice has an RDA value less than 150 which provides a crunchy prophy mouthfeel to the user during toothbrushing. The dentifrice comprises a vehicle having dispersed therein a siliceous polishing agent having a particle size distribution of about 1 to about 100 microns wherein (1) more than 25% of the particles have a size greater than about 40 microns and (2) at least about 10% of the particles of (1) have a particle size greater than about 60 microns and at least about 5% of the particles have a particle size greater than about 80 microns. In the preparation of the dentifrice, the dispersion of the silica particles in the dentifrice is accomplished under low shear conditions.

10 Claims, No Drawings

PROPHY MOUTHFEEL DENTIFRICE HAVING LOW RDA VALUE

BACKGROUND OF THE INVENTION

1. Field of the Invention

This invention relates to a dentifrice which provides a user perceivable signal of cleaning efficacy or a "prophy mouthfeel" in the oral cavity during and after use in teeth cleaning.

2. The Prior Art

Among the desirable oral sensations obtained by the use of dentifrices in the cleaning of teeth is "prophy mouthfeel" or a "dentist clean" mouth sensation. This is the same sensation one feels during and after a professional dental prophylaxis and is conveyed in a dentifrice by the polishing agent contained in the dentifrice. The mouthfeel, described as "gritty" or "crunchy", by the user is advantageous as it sends an extra signal of proof of efficacy that the dentifrice is doing more than an ordinary dentifrice.

A dentifrice known to the art to deliver a prophy mouthfeel to the user is described in U.S. Pat. No. 4,401,648. The polishing agent primarily responsible for the prophy mouthfeel is a hydrated alumina product having a particle size wherein 100% of the particles are less than 50 microns and 84% of the particles are less than 20 microns.

In consumer product evaluation tests in which panelists were asked to compare their current brand of toothpaste to the dentifrice of U.S. Pat. No. 4,401,648, the dentifrice was rated significantly higher in "cleaning teeth better".

Although the dentifrice of U.S. Pat. No. 4,401,648 exhibits strong positive ratings with respect to mouthfeel, the dentifrice had the drawback that it exhibits relatively high abrasion values, e.g. 150 units or more when subjected to Radioactive Dentin Analysis (RDA). "RDA" value is obtained by first irradiating extracted teeth in a neutron flux to make them radioactive and then brushing a dentin surface of the tooth, under standard conditions of brushing, and determining the radioactivity of the slurry surrounding the teeth after their removal.

Dentifrices having RDA values in excess of 150 raise the concern that continued use of such dentifrices will damage oral hard tissues (enamel, dentin and cementum), particularly the dentin surfaces. A second drawback to the dentifrice of U.S. Pat. No. 4,401,648, is that the stability and efficacy of certain fluoride anticaries agents advantageously incorporated in dentifrices, e.g. sodium and tin fluoride, is adversely affected by the presence of the alumina polishing agent. Therefore, it would be advantageous to formulate a dentifrice composition containing a polishing agent which would impart prophy mouthfeel with low RDA values and be compatible with a broad spectrum of fluoride anticaries agents including sodium and tin fluoride.

Siliceous polishing agents are known to be compatible with fluoride anticaries agents such as sodium and tin fluoride when incorporated as abrasives in dentifrices. U.S. patents disclosing dentifrices formulated using siliceous polishing agents include U.S. Pat. Nos. 3,689,637; 3,943,240; 3,978,205; 4,007,260; 4,108,978; 4,110,083; 4,141,969; 4,144,322; 4,663,153; 4,469,216; 4,828,833; 4,891,211 and 4,943,429.

U.S. Pat. No. 3,689,637 discloses a dentifrice composition comprised of a high molecular weight polyethylene glycol, a humectant, a silica xerogel, silica aerogel and a pyrogenic silica. The silica xerogel has an average particle diameter of 2-20 microns, the silica xerogel has an average particle diameter of about 1-3 microns and the pyrogenic silica has an average particle diameter of 15 millimicrons. The silica xerogel is present in the dentifrice at a concentration of 5-50% and the silica aerogel and/or the pyrogenic silica is present at a concentration of 0.5-20% percent.

U.S. Pat. No. 3,943,240 discloses a toothpaste containing sodium bicarbonate as the principal abrasive and a lesser amount of another compatible abrasive such as crystalline or amorphous silica having a particle size less than about 20 microns.

U.S. Pat. No. 3,978,205 discloses a dentifrice containing dehydroxylated fumed silica having a particle size of about 10-100 millimicrons.

U.S. Pat. No. 4,007,260 discloses a translucent dental cream containing finely divided synthetic amorphous silica having a particle size of about 1-30 microns.

U.S. Pat. No. 4,108,978 discloses a dentifrice containing 1-50% by weight of a silica xerogel having an average particle size of 25-50 microns.

U.S. Pat. No. 4,110,083 discloses a dentifrice having an abrasive coated with a cationic water soluble polymer whereby the abrasive is made less absorptive to therapeutic cationic agents. Illustrative of abrasives suitable for use in the dentifrice include silica xerogels having an average particle size of 1-30 microns.

U.S. Pat. No. 4,141,969 discloses a dentifrice containing a compound which provides fluoride ($N_aF$, $S_nF_2$), an amorphous silica polishing agent having an aggregate particle size of 2-20 microns and an additive which supplies calcium ions.

U.S. Pat. No. 4,663,153 discloses a tooth powder comprised of at least 50% by weight of sodium bicarbonate particles having a median particle size of 74-210 microns. Secondary abrasives such as silica gel (hydrated silica) having a particle size of 8-13 microns may also be incorporated in the dentifrice.

U.S. Pat. No. 4,689,216 discloses dentifrices containing sanguinarine of superior stability and increased uptake into dental plaque are attained by the inclusion of hydrated silica as an abrasive.

U.S. Pat. No. 4,828,833 disclose dentifrice compositions containing a siliceous dental abrasive such as amorphous precipitated silica having a particle size less than 20 microns to avoid any gritty feel.

U.S. Pat. No. 4,891,211 discloses a hydrogen peroxide-releasing dentifrice comprising a sodium bicarbonate and sodium percarbonate in a polyethylene glycol base. The sodium bicarbonate abrasive has a particle size less than about 25 microns and the median particle size is desirably less than 44 microns. Amorphous silica is included as a secondary abrasive.

U.S. Pat. No. 4,943,429 discloses a sodium bicarbonate based dentifrice gel which comprises sodium bicarbonate in an aqueous carrier with a humectant such as glycol or sorbitol. The sodium bicarbonate has a mean particle size of from 10-200 microns. Secondary abrasives such as silica gels may also be incorporated in the dentifrice gels.

A major drawback to the use of siliceous polishing agents at the concentrations, e.g., 15 to 25% by weight conventionally used in dentifrices is that at the particle size range at which a prophy mouth feel is imparted by the presence of these particles, i.e., in the 40 to 100 micron particle size range. the RDA values of the dentifrice very often exceed 150 units.

Therefore. there is a need in the art for a dentifrice which imparts a prophy mouth feel without being unduly abrasive and in which the ingredients thereof are compatible with alkali metal fluoride anticaries agents.

SUMMARY OF THE INVENTION

In accordance with the present invention, there is provided a dentifrice exhibiting low RDA values, that is, less than 150, and compatibility with fluoride anticaries agents which imparts a prophy mouth feel to the user, the dentifrice having incorporated therein a siliceous polishing agent having a particle size distribution of about 1 to about 100 microns wherein (1) more than 25% of the particles have a size greater than 40 microns and (2) at least about 10% of the particles of (1) have a size greater than about 60 microns and at least about 5% of the particles have a size greater than about 80 microns.

Preferably, the particle size distribution of the silica particles present in the dentifrice is as follows:

| Particle Size (Microns) | % in Dentifrice (Range) |
| --- | --- |
| >20 | about 50 to about 70 |
| >40 | about 10 to about 40 |
| >60 | about 1 to about 20 |
| >80 | about 5 to about 10 |

DESCRIPTION OF THE PREFERRED EMBODIMENTS

To prepare the dentifrice of the present invention, the siliceous polishing agent is dispersed in a dental vehicle which contains water and a humectant such as glycerine. sorbitol, propylene glycol or polyethylene glycol including suitable mixtures thereof. The amount of siliceous polishing agent is generally about 10 to about 40% by weight of the dentifrice; however, the effective upper limit for the siliceous polishing agent can be as high as 50% by weight but preferably is about 15 to about 25% by weight. The average particle size of the siliceous agent selected for incorporation in the dentifrice generally in the range of about 18 to about 20 microns. A preferred siliceous agent for use in the present invention which is commercially available is a synthetic amorphous silica sold by W. R. Grace & Company under the designation Sylodent 753G having an average particle size of 18.2 microns.

It is advantageous to use both water and a humectant when making the dentifrice. The total liquid content is generally over 20% by weight of the vehicle (sorbitol, which is present in admixture with water is considered a liquid for this purpose). The preferred humectants are glycerine and sorbitol. Typically, the dentifrice contains about 5 to 20% by weight of glycerine, about 10 to 30% by weight of sorbitol and about 5 to about 20% by weight water.

The vehicle may also contain a thickening or gelling agent, such as natural and synthetic gums and gum-like materials, such as Irish Moss, gum tragacanth, alkali metal (e.g. Li, K, Na) carboxymethyl cellulose and hydroxymethyl carboxymethyl cellulose, polyvinyl pyrrolidone, water soluble hydrophilic colloidal carboxyvinyl polymers such as those sold under the trademark Carbopol 934 and 940, hydroxyethyl cellulose, India gum, locust bean gum, agar, or inorganic thickeners such as colloidal silica, e.g. synthetic finely-divided silica including those sold under the trademarks Cab-O-Sil M5, Syloid 244, Syloid 266, Syloid 2, Syloid 15, and Sylox 15. The thickening and gelling portion of the vehicle is typically present in an amount up to about 10% by weight of the dentifrice and preferably within the range of about 0.5 to about 8% by weight.

The dentifrice may also contain surface-active agents, e.g. to achieve increased prophylactic action, assist achieving thorough and complete dispersion of the dentifrice throughout the oral cavity and to render the dentifrice cosmetically acceptable. Suitable types of such surfactants are water soluble salts of higher fatty acid monoglyceride monosulfates, such as sodium salts of the monosulfated monoglycerides, or hydrogenated coconut oil fatty acids, higher alkylsulfate, such as sodium lauryl sulfate, alkyl aryl sulfonates, such as sodium dodecyl benzene sulfonate, higher alkyl sulfoacetates, higher fatty acid esters of 1,2-hydroxy propane sulfonates and the substantially saturated higher aliphatic amino carboxylic acid compounds, such as those having 12 to 16 carbons in the fatty acid, alkyl or acyl radicals, and the like. Examples of the last mentioned amides are N-lauryl sarcosine, and sodium and potassium and ethanolamine salts of N-lauryl, N-myristyl or N-palmital sarcosinate, which should be free from soap.

Other suitable surfactants include non-ionic agents such as condensates of sorbitan monostearate with approximately 60 moles of ethylene oxide with propylene condensates of propylene oxide (Pluronics). It is preferred that the total amount of surfactant be from about 0.10 to about 5.0% by weight.

Any suitable flavoring or sweetening materials may be employed in formulating a flavor for the dentifrice of the present invention. Examples of suitable flavoring constituents include the flavoring oils, for example, oils of spearmint, peppermint, wintergreen, sassafras, clove, sage, eucalyptus, marjoram, cinnamon, lemon and orange, as well as sodium methylsalicylate. Suitable sweetening agents include lactose, maltose, sorbitol, sodium cyclamate, and saccharine. Suitably, flavor and sweetening agent together comprise from about 0.01 to 5 percent or more of the compositions of the instant invention. Preferably the amount of flavoring oil is above 0.5 percent, e.g. 0.8 to 1.5 percent.

The dentifrice also contains a fluoride-containing anticaries agent. There are many water-soluble inorganic salts which are suitable sources of fluoride ions.

The fluorine-providing salts used in the practice of the present invention are characterized by their ability to release fluoride ions in water and by substantial freedom from reaction with silicon compounds. Among these materials are inorganic salts, for example, sodium fluoride, potassium fluoride, cuprous fluoride, a tin fluoride such as stannous fluoride or stannous chlorofluoride, sodium fluorosilicate, ammonium fluorosilicate, sodium monofluorophosphate, alumina mono- and di-fluorophosphate. Alkali metal and tin fluorides, such as sodium fluoride, stannous fluoride, sodium monofluorophosphate and mixtures thereof, are preferred.

Any suitable minimum amount of the fluoride compound may be used, but it is preferable to employ sufficient compound to release from about 0.05% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 0.5% by weight.

Other agents suitable for incorporation in the dentifrice products of the present invention include synthetic anionic linear polymeric polycarboxylates which are employed in the form of their partially or preferably fully neutralized water soluble alkali metal (e.g. potassium and preferably sodium) or ammonium salts. Preferred are 1:4 to 4:1 copolymers of maleic anhydride or acid and a polymerizable ethylenically unsaturated monomer, preferably a lower alkyl vinyl ether such as methoxyethylene, having a molecular weight of about 30,000 to about 1,000,000 available commercially from GAF Corporation under the trademark Gantrez. The polycarboxylates are incorporated in the dentifrice compositions of the present invention at a concentration of about 0.5 to about 20% by weight and preferably about 1.0 to about 8.0 percent by weight.

Anti-bacterial agents such as 2,4,4'-trichloro-2'-hydroxydiphenyl ether (Triclosan), 5,5'-dichloro-2,2'-dihydroxydiphenyl methane; (Dichlorophene), 2,2'-dihydroxy-3,5,6,3',5',6'-hexachloro diphenylmethane; (Hexachlorophene), and 3,3'-dibromo-5,5'-dichloro-2,2'-dihydroxy-diphenylmethane (Bromochlorophene), may be incorporated in the dentifrice at a concentration of about 0.01 to about 2% by weight.

Anti-tartar agents such as a dialkali or tetra-alkali metal pyrophosphate salt such as $Na_4P_2O_7$, $K_4P_2O_7$, $Na_2K_2P_2O_7$, $Na_2H_2P_2O_7$ and $K_2H_2P_2O_7$ may also be incorporated in the dentifrice products of the present invention at a concentration of about 0.5 to about 15% by weight and preferably 1.0 to about 10% by weight.

Other materials may be included in the dentifrice such as coloring or whitening agents such as titanium dioxide and preservatives such as sodium benzoate at concentrations of 0.5 to 2% by weight of the dentifrice.

In preparing the dentifrice compositions of the present invention the ingredients thereof are preferably combined in a series of steps so that fragmentation of the relatively soft silica particles is minimized to insure that the incorporation of these particles in the dentifrice will impart thereto the desired prophy mouthfeel property to the dentifrice.

Thus, it has been determined that conventional procedures used to prepare dentifrice formulations can result in high viscosity compositions which require high shear mixing of the ingredients to prepare a uniform dispersion. Prior art procedures for the preparation of dentifrices generally involve first preparing a dispersion of thickening agents and "unwet" (no water presence) humectants followed by wet humectants (e.g. sorbitol) and water soluble inorganic salts such as sodium fluoride. Thereafter water is added to hydrate the thickening agents and swell the composition to impart "body" thereto. The polishing agent is then added to the swelled composition and mixed under high shear conditions to evenly disperse the polishing agent in the swelled composition. This high shear mixing has been found by the present inventors to cause extensive fragmentation of the silica particles resulting in a loss of prophy mouthfeel characteristics in the finally formulated dentifrice.

To avoid fragmentation of the silica particles during the mixing process used in dispersing the ingredients of the dentifrice of the present invention, the dentifrice is prepared in a specific sequence of steps in order that the dispersion of the silica particles in the dentifrice formulation is accomplished under low shear conditions. Thus the ingredients of the dentifrice are combined according to the present invention in the following sequential steps:

(1) admix together water, all wet humectants and water soluble inorganic salts to prepare a low viscosity, e.g., up to about 40 centipoise/second (cps), aqueous solution;

(2) admix with the so prepared aqueous solution the siliceous polishing agent, thickeners, surfactant and flavor to prepare a slurry of the polishing agent; and (3) admixing with the so prepared slurry the remaining ingredients, e.g., gums and unwet humectants such as glycerin.

Adding the glycerin/gum components to the slurry as the last step in the preparation of the dentifrice provides a uniform dispersion with a minimum fragmentation of the silica particles.

The following Example is given to illustrate the invention in further, but non-limiting detail:

EXAMPLE

A dentifrice was prepared using the following ingredients:

| PART | INGREDIENTS | % |
|---|---|---|
| A | Sorbitol non-crystallizing (70%) | 19.50 |
| | Gantrez liquid (1%) | 15.00 |
| | Titanium Dioxide | 0.5 |
| | Sodium Hydroxide (50%) | 1.0 |
| | Sodium Fluoride | 0.243 |
| | Sodium Saccharin | 0.30 |
| | Deionized Water | 13.00 |
| B | Sylodent 753G | 18.00 |
| | Sylox 15 | 7.00 |
| | Flavor | 1.00 |
| | Triclosan | 0.30 |
| | Sodium Lauryl Sulfate | 1.5 |
| C | Glycerin (99.3%) | 10.00 |
| | Propylene Glycol | 0.50 |
| | Carboxymethyl Cellulose | 1.25 |

The above ingredients were processed according to the following sequential steps:

(1) The ingredients of Part A were mixed at 32° C. for 20 minutes and placed in a vertical cylindrical container equipped with a Dopp mixer which has a series of intermeshing counter-rotating radially disposed mixing rods located all along its height. Part A was an aqueous solution having a viscosity of about 40 cps. Part B was added to Part A in the Dopp mixer while mixing at the high speed setting for about 5 minutes to prepare a slurry of the Sylodent 753G synthetic amorphous silica particles. Thereafter the components of Part C were added. A vacuum of 30 inches mercury was applied and the maximum speed applied. After mixing at maximum speed for 20 minutes, the mixture was vented to the atmosphere and the glycerine, propylene glycol and carboxymethyl cellulose dispersion of Part C was added to the mixing vessel at a slow speed setting. After the addition of these final components of the dentifrice composition, a vacuum of 30 inches of mercury was applied and the mixture kept under vacuum for an additional 10 minutes while mixing at high speed. At the conclusion of this mixing step, the vessel was vented to the atmosphere and the dentifrice composition collected from the vessel.

The so prepared dentifrice product was a smooth cream having an RDA value in the range of 80 to 120. When evaluated for prophy mouthfeel the users who brushed their teeth with the dentifrice reported that the dentifrice exhibited excellent crunch or grit while brushing and was easily rinsed away after brushing. The users further indicated that after brushing, their teeth had a superior "clean feeling."

The dentifrice was submitted to particle size identification using an HAC/ROYCO Model 4300 particle size analyzer instrument to count the number of silica particles in the range of >100 microns down to >20 microns in the dentifrice. The particle size distribution in the dentifrice is summarized in Table I. For purposes of comparison the particle size distribution of the original synthetic amorphous silica particles before addition to the dentifrice is also summarized.

TABLE I

| Particle Size (microns) | % of Silica Particles in Dentifrice after mixing | % of Silica Particles Before Addition to Dentifrice |
|---|---|---|
| >20 | 68.44 | 58.55 |
| >40 | 30.29 | 16.17 |
| >60 | 16.05 | 6.59 |
| >80 | 6.22 | 1.39 |

For purposes of further comparison, the procedure of the Example was repeated with the exception that the order of addition of the dentifrice ingredients to the mixture was as follows:

| | % |
|---|---|
| Part 1 | |
| Glycerin (99.3%) | 10.00 |
| Propylene Glycol | 0.50 |
| Carboxymethyl Cellulose | 1.25 |
| Part 2 | |
| Sorbitol non-crystallizing (70%) | 19.50 |
| Sodium Saccharin | 0.30 |
| Sodium Fluoride | 0.243 |
| Titanium dioxide | 0.50 |
| Deionized Water | 13.00 |
| Part 3 | |
| Gantrez liquid (1%) | 15.00 |
| Sodium Hydroxide (50%) | 0.80 |
| Part 4 | |
| Sylodent 753G | 18.00 |
| Sylox 15 | 7.0 |
| Flavor | 0.95 |
| Triclosan | 0.30 |
| Part 5 | |
| Sodium Lauryl Sulphate | 1.50 |

When evaluated for prophy mouthfeel, the users who brushed their teeth with the comparative dentifrice reported that the comparative dentifrice was perceived as having no prophy mouthfeel and failed to provide the clean mouthfeel sensation experienced by the users with the dentifrice of the Example.

The particle size distribution in the comparative dentifrice is summarized in Table II below:

TABLE II

| Particle Size (microns) | % of Silica Particles in Dentifrice | % of Silica Particles Before Addition to Dentifrice |
|---|---|---|
| >20 | 47.07 | 58.55 |
| >40 | 1.99 | 16.17 |
| >60 | 0.05 | 6.59 |
| >80 | 0 | 1.39 |

What is claimed is:

1. In a method of making a dentifrice cream having an RDA value less than 150 which provides a crunchy prophy mouthfeel to the user thereof the improvement comprising avoiding extensive fragmentation of the relatively soft silica particles caused by high shear mixing comprising the steps of first admixing water, wet humectants, and water soluble inorganic salts to prepare an aqueous solution, admixing under low shear conditions the so prepared aqueous solution with a relatively soft siliceous polishing agent and thickeners to prepare an aqueous slurry of the polishing agent and then admixing with the slurry unwet humectants and gums and continuing the low shear admixing until the admixed composition has dispersed therein at least 10% by weight of a siliceous polishing agent having a particle size distribution of about 1 to about 100 microns wherein (1) more than 25% of the particles have a size greater than about 40 microns and (2) at least about 12% of the particles of (1) have a particle size greater than about 60 microns and at least about 5% of the particles have a size greater than about 80 microns.

2. The method of claim 1 wherein the silica particle size distribution in the dentifrice is as follows:

| Particle Size | % of Total Silica in Dentifrice |
|---|---|
| >20 | about 50 to about 70 |
| >40 | about 10 to about 40 |
| >60 | about 1 to about 20 |
| >80 | about 5 to about 10 |

3. The method of claim 1 wherein the siliceous polishing agent is a synthetic amorphous silica.

4. The method of claim 1 wherein the siliceous polishing agent is incorporated in the dentifrice at a concentration of about 10 to about 40 percent by weight.

5. The method of claim 1 wherein the siliceous polishing agent is incorporated in the dentifrice at a concentration of about 15 to about 25 percent by weight.

6. A dentifrice cream composition having an RDA value less than 150 which provides a crunchy prophy mouthfeel to the user thereof during toothbrushing, the dentifrice comprising a vehicle having dispersed therein at least about 10% by weight of a siliceous polishing agent that is relatively soft and fragments under high shear having a particle size distribution of about 1 to about 100 microns wherein (1) more than 25% of the particles have a size greater than about 40 microns and (2) at least about 10% of the particles of (1) have a particle size greater than about 60 microns and at least about 5% of the particles have a particle size greater than about 80 microns, produced in accordance with the process of claim 1.

7. The dentifrice composition of claim 6 wherein the silica particle size distribution in the dentifrice is as follows:

| Particle size | % of silica particles in dentifrice |
|---|---|
| >20 | about 50 to about 70 |
| >40 | about 10 to about 40 |
| >60 | about 1 to about 20 |
| >80 | about 5 to about 10 |

8. The dentifrice composition of claim 6 wherein the siliceous polishing agent is a synthetic amorphous silica.

9. The dentifrice of claim 6 wherein the siliceous polishing agent is incorporated in the dentifrice at a concentration of about 10 to about 40 percent by weight.

10. The dentifrice of claim 6 wherein the siliceous polishing agent is incorporated in the dentifrice at a concentration of about 15 to about 25 percent by weight.

* * * * *